(12) United States Patent
Solzbacher et al.

(10) Patent No.: US 8,521,303 B2
(45) Date of Patent: Aug. 27, 2013

(54) IN VIVO IMPLANTABLE COIL ASSEMBLY

(75) Inventors: Florian Solzbacher, Salt Lake City, UT (US); Reid R. Harrison, Salt Lake City, UT (US); Richard A. Normann, Park City, UT (US); Sohee Kim, Salt Lake City, UT (US); Michael Töpper, Berlin (DE); Hans-Hermann Oppermann, Berlin (DE); Klaus Buschick, Berlin (DE); Matthias Klein, Berlin (DE)

(73) Assignee: University of Utah Reasearch Foundation, Salt Lake City, UT (US)

( * ) Notice: Subject to any disclaimer, the term of this patent is extended or adjusted under 35 U.S.C. 154(b) by 1647 days.

(21) Appl. No.: 11/880,103

(22) Filed: Jul. 17, 2007

(65) Prior Publication Data

US 2008/0021525 A1    Jan. 24, 2008

Related U.S. Application Data

(60) Provisional application No. 60/831,557, filed on Jul. 17, 2006, provisional application No. 60/842,770, filed on Sep. 6, 2006, provisional application No. 60/919,580, filed on Mar. 22, 2007.

(51) Int. Cl.
*A61N 1/04* (2006.01)

(52) U.S. Cl.
USPC ............................... 607/116; 600/372

(58) Field of Classification Search
USPC ........................................... 600/372; 607/116
See application file for complete search history.

(56) References Cited

U.S. PATENT DOCUMENTS

| | | | |
|---|---|---|---|
| 4,143,661 A | | 3/1979 | LaForge et al. |
| 4,441,498 A | | 4/1984 | Nordling |
| 4,665,896 A | | 5/1987 | LaForge et al. |
| 5,312,674 A | | 5/1994 | Haertling et al. |
| 5,411,730 A | * | 5/1995 | Kirpotin et al. ............ 424/9.322 |
| 5,528,222 A | | 6/1996 | Moskowitz et al. |
| 5,741,316 A | | 4/1998 | Chen et al. |
| 6,179,772 B1 | * | 1/2001 | Blackwell ..................... 600/13 |
| 6,445,956 B1 | | 9/2002 | Laird et al. |
| 6,850,803 B1 | * | 2/2005 | Jimenez et al. ................ 607/61 |
| 6,876,056 B2 | | 4/2005 | Tilmans et al. |
| 6,939,299 B1 | * | 9/2005 | Petersen et al. .............. 600/398 |
| 2002/0055763 A1 | * | 5/2002 | Zarinetchi et al. ............. 607/61 |
| 2005/0288743 A1 | * | 12/2005 | Ahn et al. ....................... 607/61 |
| 2006/0241354 A1 | * | 10/2006 | Allen ............................. 600/300 |

* cited by examiner

*Primary Examiner* — Joseph Dietrich
(74) *Attorney, Agent, or Firm* — Thorpe North & Western LLP

(57) ABSTRACT

An in-vivo implantable coil assembly includes a planar coil having at least one coil layer formed from conductive traces disposed in or on a polymer matrix. A ferrite platelet is bonded to a surface of the polymer matrix. Methods of making and using the in-vivo implantable coil assembly are also disclosed.

28 Claims, 4 Drawing Sheets

IN VIVO IMPLANTABLE COIL ASSEMBLY

RELATED APPLICATIONS

This application claims the benefit of U.S. Provisional Patent Application Ser. No. 60/831,557, filed Jul. 17, 2006, and entitled "Integrated Wireless Neural Interface for Chronic Recording and Stimulation," U.S. Provisional Patent Application Ser. No. 60/842,770, filed Sep. 6, 2006 and entitled "In Vivo Implantable Coil Assembly", and U.S. Provisional Patent Application Ser. No. 60/919,580, filed Mar. 22, 2007, and entitled "In Vivo Implantable Coil Assembly" which are each hereby incorporated by reference.

GOVERNMENT RIGHTS

This invention was made with government support under Grant # NS042362 awarded by the National Institutes of Health. The government has certain rights to this invention.

BACKGROUND

1. Field of the Invention

The present invention relates generally to in-vivo implantable electronic devices. More particularly, the present invention relates to an in-vivo implantable coil assembly.

2. Related Art

Implantable electronic devices present many unique challenges in terms of reliability, environment, and size limitations. For example, the in vivo environment can present materials and temperatures which are quite corrosive. Further, implanted devices may provoke immune system reactions and cause other problems. Certain materials can aggravate undesired responses to the living organism in which they are implanted. In general, biocompatible materials are those which have the ability to perform with an appropriate host response in a specific application. In general, implantable electronic devices use biocompatible materials, but this tends to limit the choices of materials available. For example, lead tends to be toxic and therefore is highly undesirable for use in living organisms. Accordingly, constructing electronic devices with desired performance levels which are suitable for in vivo implantation is challenging.

SUMMARY

The present invention is directed generally towards in-vivo implantable coil assemblies, methods of making in-vivo implantable coil assemblies, and methods of use for in-vivo implantable coil assemblies.

In accordance with an embodiment of the present invention, an in-vivo implantable coil assembly includes a planar coil having at least one coil layer formed by conductive traces disposed in a polymer matrix and includes exposed electrical contacts for electrical connection to the coil layer or layers. In addition, a ferrite platelet can be bonded to a surface of the polymer matrix.

Another embodiment of the present invention is a method of making an in-vivo implantable coil assembly. The method can include coating a sacrificial separation layer onto a temporary substrate. A polymer layer can be deposited onto the separation layer, and a thin film coil fabricated on the polymer layer. Electrical contacts can be formed on a top surface of the thin film coil. The polymer layer can be separated from the temporary substrate and bonded to a ferrite substrate to form a planar coil assembly.

The in-vivo implantable coil assembly can be mounted to a neural interface assembly to form an integrated neural probe in accordance with another embodiment of the present invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1A:
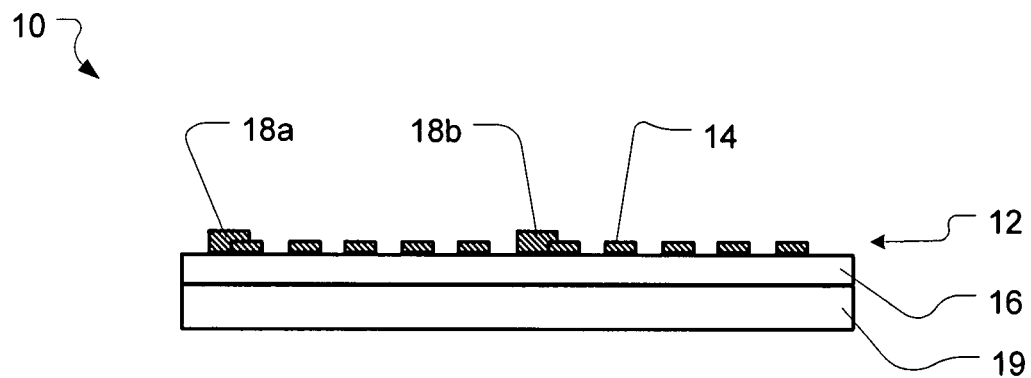
FIG. 1(a) is a side cross-sectional view illustration of a coil assembly in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

In describing embodiments of the present invention, the following terminology will be used.

The singular forms "a," "an," and "the" include plural referents unless the context clearly dictates otherwise. Thus, for example, reference to "a coil" includes reference to one or more of such coils, reference to "a layer" includes reference to one or more of such layers, and reference to "depositing" includes one or more of such steps.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "less than 20 micrometers" should be interpreted to include not only the explicitly recited values of about 20 micrometers, but also include individual values and sub-ranges within the indicated range. Thus, included in this numerical range are individual values such as 15, 10, and 5 micrometers, and sub-ranges such as from 5-10, from 5-20, and from 10-20 micrometers, etc. This same principle applies to ranges reciting only one numerical value and should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art.

As introduced above, there are a number of challenges faced in designing in-vivo implantable electronic devices. One particular challenge is providing power to operate an implanted device. One approach to powering the implanted device is to couple power into the device inductively. In such an approach, a coil assembly is included within the implanted device and configured to extract power from an externally generated magnetic field. While a larger coil can help to provide higher levels of power extraction, it is generally desirable for in-vivo devices to be relatively small. As a particular example, an implantable neural interface assembly may have dimensions of less than about 1 centimeter per side, or more particularly, less than about 5 millimeters per side. Accordingly, small, yet efficient, coils are desirable.

When building small coils, one way to provide high efficiency is by including a high permeability material. For example, coils can be fabricated using low temperature co-fired ceramic (LTCC) techniques. The ceramic material can provide high permeability, and the coil can be fabricated directly onto the ceramic material, for example, by screening a conductive paste onto the ceramic material before firing. Unfortunately, the LTCC process provides limited resolution, and it is difficult to fabricate coils using very small traces. In particular, poor reliability may be obtained with very small traces due to the roughness of the ceramic materials. Accordingly, LTCC techniques may provide a limited number of coil turns to be provided within small coil diameters.

Fabrication of coils using lithographic techniques, for example, on a polymer material, can overcome the above disadvantages. However, polymer materials provide generally low permeability, and thus coil inductance, quality factor, and coupling is generally lower than desired.

Figure 1B:
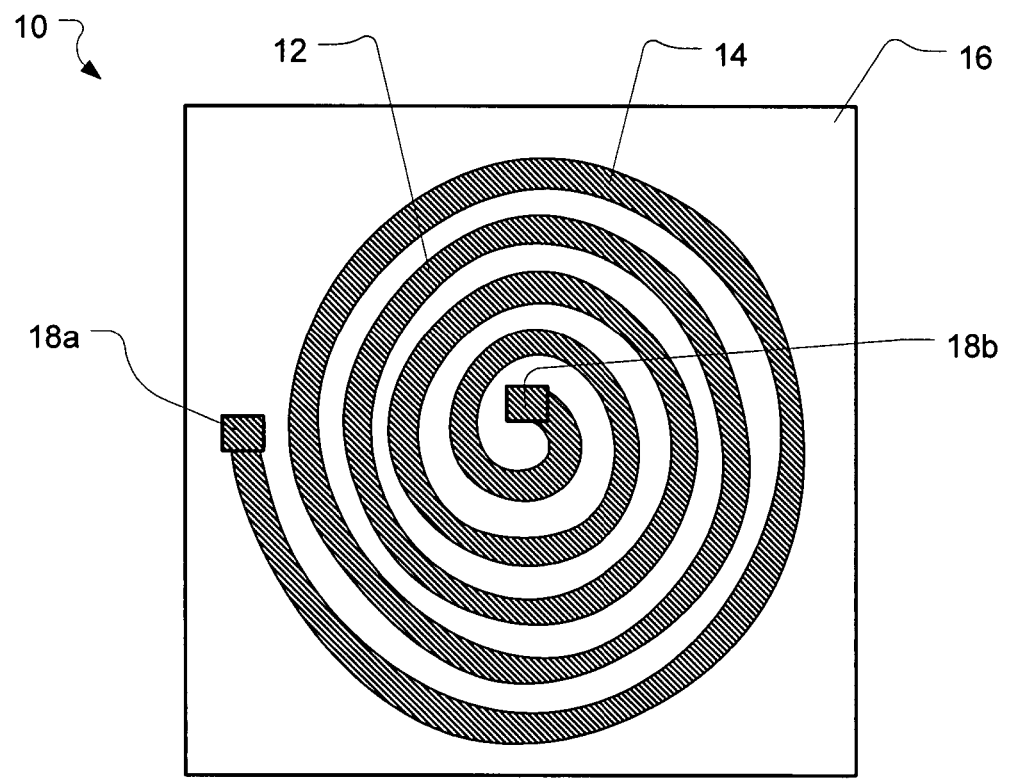
FIG. 1(b) is a top view illustration of the coil assembly of FIG. 1(a)

Accordingly, embodiments of the present invention can help to overcome the aforementioned difficulties. In particular, a first embodiment of the present invention is an in-vivo implantable coil assembly as illustrated in FIG. 1(a) and FIG. 1(b). The coil assembly, shown generally at 10, includes a planar coil having at least one planar coil layer 12 formed by conductive traces 14 disposed in a polymer matrix 16. For example, the polymer matrix can include, consist of, or consist essentially of materials such as polyamide, polyimide, benzocyclobutene, composites thereof, and combinations thereof. The polymer material helps to provide a smooth surface on which the coil layer can be formed.

The planar coil includes exposed electrical contacts 18a, 18b for electrical connection to the conductive traces. Non-limiting examples of materials which are suitable for forming the conductive traces and/or electrical contacts can include, consist of, or consist essentially of gold, silver, chromium, platinum, titanium, iridium, conductive polymers (e.g. polyacetylenes, polypyrroles, polyanilines, polythiophenes, polyfluorenes, etc.), other conductive materials, combinations, or alloys thereof. In one specific embodiment, the conductive traces can consist essentially of a single conductive material. In another aspect, the conductive traces can consist essentially of gold. Although almost any functional arrangement can be designed, the electrical contacts can typically be arranged in a desired pattern which corresponds to electrical connections on a neural interface assembly to allow mounting of the coil assembly to a neural interface assembly to provide electrical connections between the coil assembly and the neural interface assembly.

The coil assembly 10 includes a ferrite platelet 19 bonded to a surface of the polymer matrix as shown in FIG. 1(a). The ferrite platelet can function as a high permeability structure which can generally be in the form of a layer or segment of material. The ferrite platelet can include, consist of, or consist essentially of a ferromagnetic material. For example, the ferrite platelet can be formed from or include a low temperature co-fired ceramic (LTCC) material. The ferrite platelet can also be formed from or include a plurality of colloidal ferrite particles within a non-conducting medium. For example, the non-conducting medium can be a flexible material, such as a polymer. A flexible material can provide advantages in helping to minimize stress in the completed neural interface assembly. The colloidal ferrite particles can be, for example, nanoparticles. Ferrite materials are electrically non-conductive ferromagnetic materials that conduct magnetic flux well and thus have high relative magnetic permeability. For example, a relative permeability of greater than about 200 is desirable in helping to provide a high inductance for the planar coil. For example, a coil having an outer diameter of about 5 millimeters can achieve an inductance of about 75 uH and a quality factor (Q) of greater than about 10. In general, inductances in the range of about 5 to about 75 uH can be achieved, depending on the coil configuration (conductor line width, conductor spacing, metal thickness, fill of coil turns within the outer diameter, single or double layer coil, etc.). High inductance is desirable to allow for efficient coupling when using the planar coil as a secondary in a distributed transformer to allow for inductive current coupling. This allows more power transfer when the planar coil is used in inductive power coupling applications. For example, the coil assembly can be used for powering in-vivo electronic circuitry by inductively coupling power into the planar coil from a primary coil external to the body. Suitable ferrite materials can include, but are not limited to, iron oxides such as Hematite ($Fe_2O_3$), Magnetite ($Fe_3O_4$), MnZn, NiZn, MgZn, barium ferrite, strontium ferrite, other metal oxides, or combinations and composites thereof.

An additional advantage provided by the ferrite platelet 19 is shielding the coil assembly 10 from underlying circuitry or neighboring interference. For example, when the coil assembly is in proximity to a silicon microchip within a neural probe localized current fluctuations can reduce the consistency and/or efficiency of the coil. The ferrite platelet can help to prevent eddy currents in the underlying silicon microchip circuitry that would reduce the effective inductance and increase series resistance of the coil. The ferrite platelet also helps to shield the underlying circuitry from the magnetic fields used to power the coil, helping to avoid upset to sensitive circuitry within the silicon microchip. Thus, the ferrite platelet can act as a barrier to interference in both directions across the assembly.

The ferrite platelet 19 can be quite thin to maintain a low profile for the coil assembly, helping to keep the overall size of implanted electronics using the coil assembly small. For example, the platelet can have a thickness of about 200 micrometers, or generally about 50 to about 500 micrometers, and more generally about 100 to about 300 micrometers.

The polymer layer 16 helps to insulate the coil layer(s) 12 from the ferrite platelet 19, and also provides mechanical protection of the coil layers during fabrication. The polymer layer may have any functional thickness which provides sufficient insulation. The polymer layer also helps to provide an even surface on which the coil layers can be fabricated. Accordingly, the thickness and viscosity of the polymer layer are sufficient to enable the desired resolution during lithographic (or other) fabrication of the coil layers. As a general guideline, thickness of about 10 micrometers, or generally about 5 to about 30 micrometers, and more generally about 1 to about 100 micrometers can be suitable. Of course, other thicknesses may be used to advantage depending upon the particular application. The overall diameter of the coil can be about 5 millimeters, or generally about 2 to about 7 millimeters, or more generally about 1 to about 10 millimeters. The overall dimensions of the coil assembly are a function of the desired electrical characteristics and performance of the coil, power transmission efficiency of the coil, and mechanical robustness.

The coil layer 12 is typically planar in that the turns of the coil are located substantially within a common plane in the polymer matrix. For example, the coil may be in a spiral configuration as shown, although other configurations, including for example, rectangular, hexagonal, octagonal, and the like, may also be used.

In one embodiment of the present invention, the coil can be fabricated on a temporary substrate and then attached to the ferrite platelet 19 as described further below. Building the coil on or within a polymer layer provides advantages in that photolithographic processes (as described further below) can be used to provide fine pitch lines, helping to provide for a high number of turns, and thus high impedance, in a relatively small area. The polymer layer helps to even out surface roughness that is present on ferromagnetic materials, such as LTCC materials, that would make achieving fine pitch lines difficult. For example, the turns of the coil can have a thickness of about 20 micrometers or less, and can have a width of about 20 micrometers or less. Of course, other dimensions may be used to advantage depending upon the particular application. Achieving such dimensions using screen printing processes on LTCC material is difficult. Accordingly, fabrication on the polymer layer enables larger numbers of coil turns and larger numbers of layers to be fabricated as compared to an LTCC thick film process. Although the number of coil turns can vary considerably depending on the configuration, from about 5 to about 120 coil turns can be fabricated in a 5 millimeter×5 millimeter polymer matrix. More particularly, a coil having about 40 to about 70 coil turns can be desirable to achieve sufficient impedance.

Although the coil layer 12 is shown in FIGS. 1(a) and 1(b) as fabricated on top of the polymer matrix 16, the coil layer may be embedded within the polymer matrix. Embedding the conductive traces 14 entirely within the polymer matrix can help to provide a more uniform top surface that can provide for easier encapsulation with other materials to enhance biocompatibility and to improve packaging. For example, a neural probe incorporating the coil assembly may be ultimately encapsulated within parylene C and/or silicon carbide.

Figure 2:
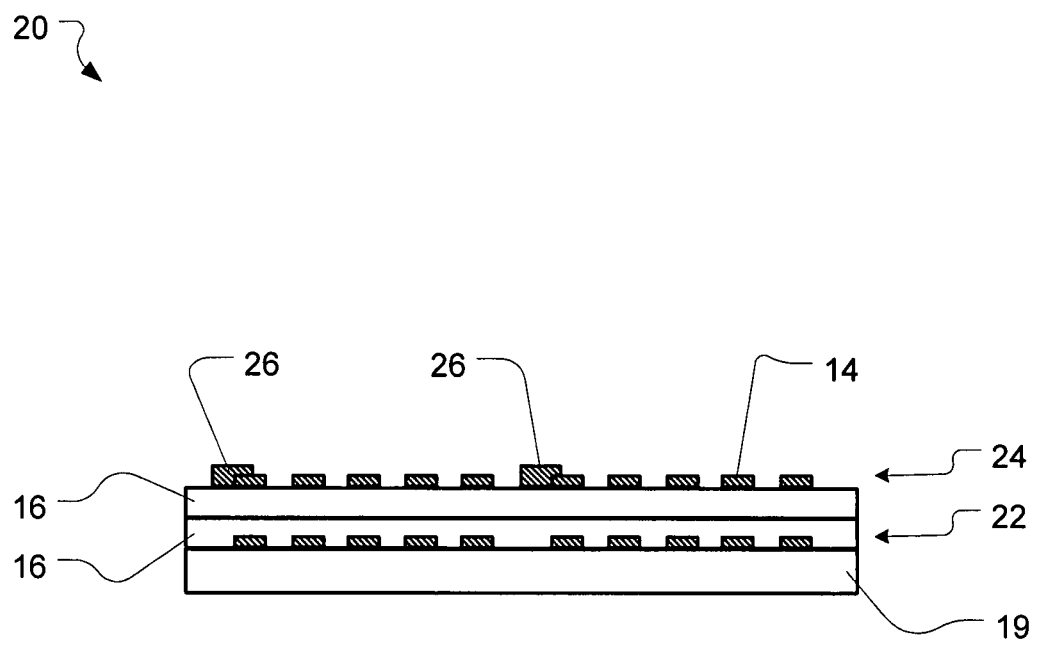
FIG. 2 is a side cross-sectional view of a coil assembly in accordance with another embodiment of the present invention.

The planar coil assembly can have a plurality of layers, including a plurality of coil layers. For example, FIG. 2 illustrates a coil assembly 20 having a first coil layer 22 and a second coil layer 24. The coil layers are stacked on top of each other, separated by polymer material 16 to provide electrical (ohmic) isolation between the layers. Generally, the stacking can be in a direction perpendicular to the plane of the coils. Coil layers can be connected together, for example, through additional conductive traces. Each of these layers can be sequentially deposited or formed. Alternatively, segments of the assembly can be independently formed and then assembled having suitable electrical contacts to allow an electrical path and communication to each coil, respectively.

In another embodiment, separate electrical contacts 26 can be provided for each end of each coil layer enabling the alternative connection of the coil layer in either series or parallel arrangement. Such an arrangement can be helpful, for example, in a situation where the environment in which the coil is to be implanted is unknown or variable and it is desirable to be able to adjust the impedance of the coil. Thus, by providing for two or more coil layers, the overall coil assembly impedance can be variably adjusted to a desirable level given a specific scenario. Further, although FIG. 2 illustrates a stacked configuration, other configurations can also be suitable. For example, multiple coils may be formed in a common plane on either a common substrate, or distinct substrates, which are then connected together in either series or parallel as previously discussed. This configuration would allow for a decrease in thickness in the assembly and may be desirable for some applications which require a low thickness profile.

The number of turns (windings) of the coil, the number coil layers, width of the conductive traces, spacing of the conductive traces, amount of fill of the coil spiral, spacing between the coil layers and ferrite platelet, spacing of coil layers, and other parameters can all be varied to achieve a desired inductance, quality factor, and parasitic capacitance. It will be appreciated that the resulting performance is also a function of the frequency of operation. Accordingly, experimental results for various coil arrangements in accordance with embodiments of the present invention are provided within U.S. Provisional Patent Application Ser. No. 60/831,557 referenced above and incorporated herein.

One example of manufacturing an implantable coil assembly will be described in conjunction with the flow chart of FIG. 3 which illustrates a method of making a coil assembly, although other ways of making the implantable coil assembly can be used. The implantable coil assembly can be fabricated on a temporary substrate, such as a silicon wafer, as used for semiconductor fabrication. The temporary substrate may be reusable, in that the silicon wafer is left substantially undamaged or modified by the manufacturing process about to be described. A first step of the process is coating 32 a sacrificial separation layer onto the temporary substrate. The sacrificial separation layer will allow later separation of the coil assembly from the temporary substrate. The sacrificial separation layer may be, for example, a non-filled thermoplastic polymer, such as Staystik® 301 available from Alpha Metals Inc., or any other temporary and removable material (e.g. via carbonizing, physical adherence prevention by powders, etc.)

A next step is depositing 34 a polymer layer onto the separation layer. The polymer layer can be various materials, for example as described above. As a particular example, the polymer layer may be polyimide spin coated onto the wafer in a liquid form and then cured.

In general, coating and depositing materials can be performed by any process that grows, coats, or otherwise transfers a material onto the device under construction. For example materials can coated or deposited by spin coating, dip coating, sputtering, jetting, screening, physical vapor deposition (PVD), chemical vapor deposition (CVD), electrochemical deposition (ECD), molecular beam epitaxy (MBE), atomic layer deposition (ALD), and similar processes.

On top of the polymer layer, a thin film coil is fabricated 36, and contacts are formed 38 on a top surface of the thin film coil. For example, conductive material may be sputtered onto the polymer layer and patterned using lithography. Contacts can be formed by electroplating or electroless plating an exposed portion of the conductive traces. The coil is a thin film coil as the vertical dimensions of the coil can be on the order of micrometers, for example as described above. The thin film coil can be a multilayer coil formed by repeating steps of forming a metallization layer, patterning the metallization layer to form a coil layer, depositing additional polymer to embed the coil layer. For example, one, two, or more coil layers can be formed to obtain a stacked configuration. The coil layers can include electrical interconnections to a previously formed metallization layer to provide connections between coil layers or to provide connections from individual coil layers to electrical contacts on the top surface of the thin film coil.

Patterning can include changing the shape of deposited materials, for example by using lithography. In lithography, the device is coated with a photoresist, the photoresist exposed through a mask. Either negative or positive photoresist may be used. Either unexposed (negative photoresist) or exposed (positive photoresist) regions are washed away by a developer solution, and etching or other processing used to remove the deposited material from the regions that have been revealed by removal of the photoresist. The photoresist can be placed over the material to be patterned, and etching performed to remove undesired material. Alternately, the photoresist can be placed under the material to be pattern, and after deposition of the material, the photoresist dissolved allowing the undesired material to be lifted off. Various lithography techniques are known and used in the semiconductor processing arts and can vary from the above sequence while still being effective for use in connection with the present invention.

Etching can be performed, for example, by wet etching or dry etching such as reactive ion etching (RIE), plasma etching, sputter etching, solution etching or the like. In one specific embodiment, etching can be performed by RIE.

Figure 4:
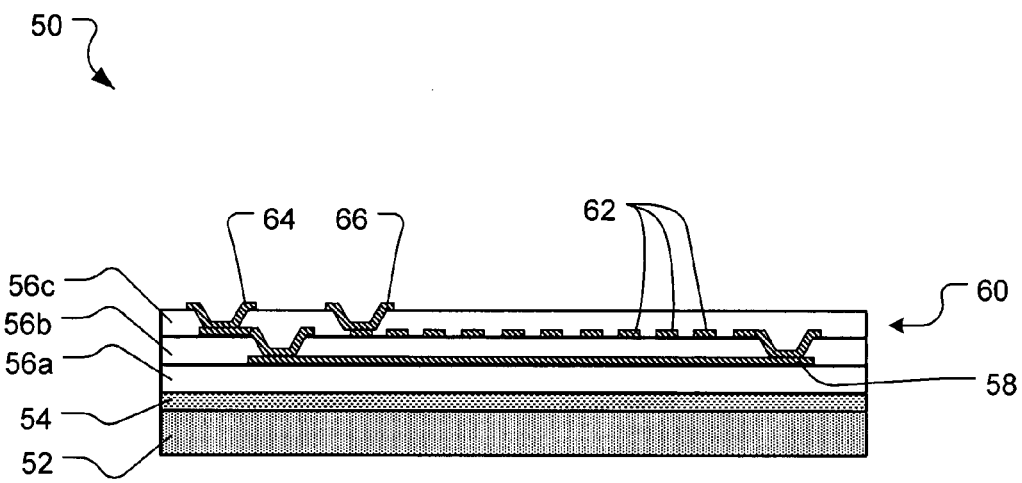
FIG. 4 is a side cross-sectional view of a coil assembly in the process of being fabricated in accordance with an embodiment of the present invention.

Multiple layers of polymer and conductive traces can also be fabricated to provide interconnection or routing of conductors. For example, FIG. 4 illustrates a cross section of a coil assembly 50 during fabrication showing the temporary substrate 52, sacrificial layer 54, and polymer layers 56a, 56b, 56c. A single layer coil 60 is between polymer layers 56b and 56c formed by conductive traces 62. Conductive material 58 underneath the coil provides routing to connect one end of the coil to a first electrical contact 64. A second electrical contact 66 is connected via conductive trace 66 to the other end of the coil.

Figure 3:
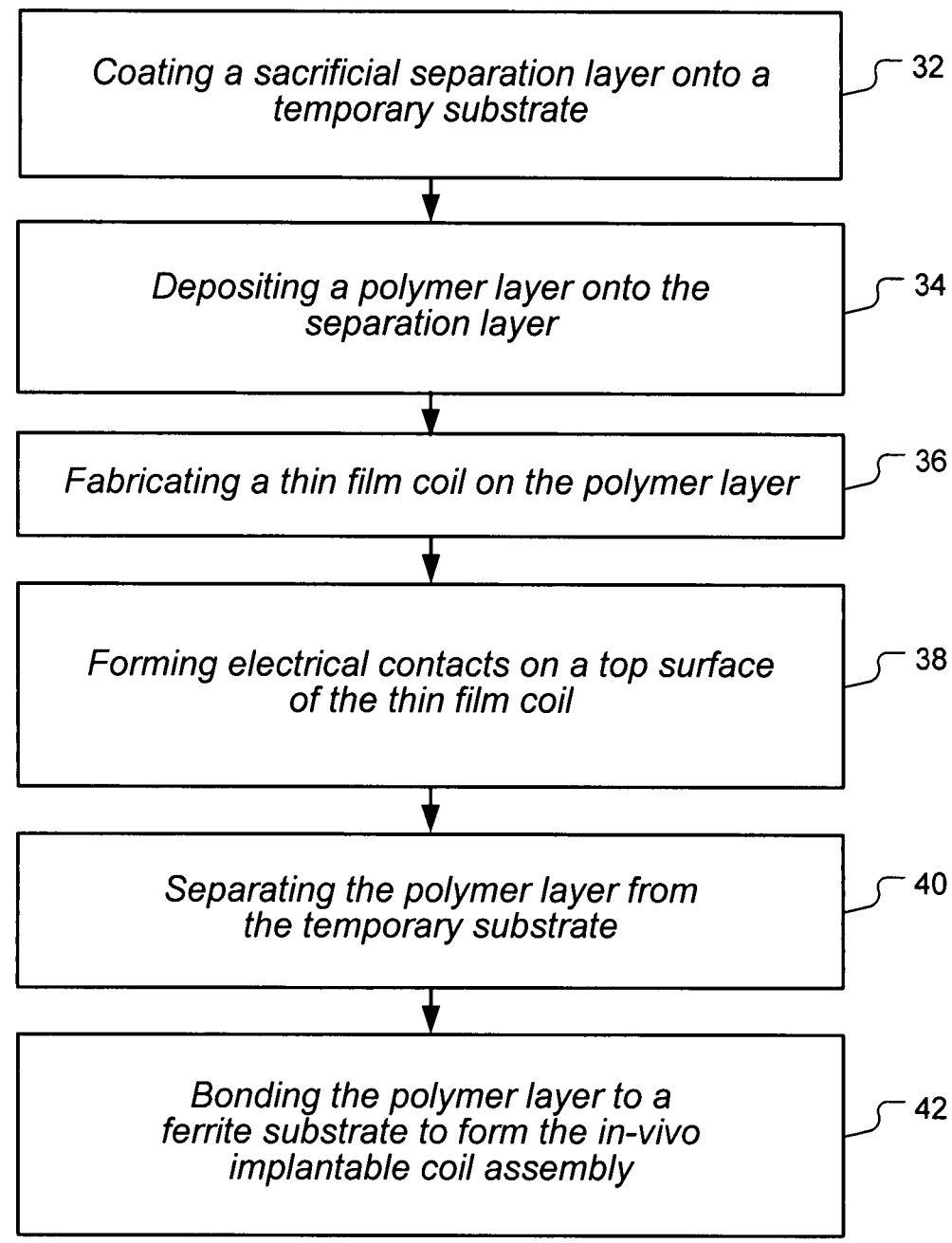
FIG. 3 is a flow chart of a method of making a coil assembly in accordance with an embodiment of the present invention.

Returning to the flow chart of FIG. 3, following the fabrication 36 of the thin film coil and forming 38 of electrical contacts, the thin film coil can be removed from the temporary substrate. This can be performed by separating 40 the polymer layer from the substrate, for example, by chemically and/or thermally removing the separation layer. For example, chemical removal can be performed by dissolving or otherwise degrading the separation layer. The polymer layer can then be bonded 42 to a ferrite substrate to form the in-vivo implantable coil assembly. Bonding may be performed by gluing the polymer layer to the ferrite substrate using a suitable adhesive, including for example, epoxy resin although other adhesives can also be used.

Figure 5:
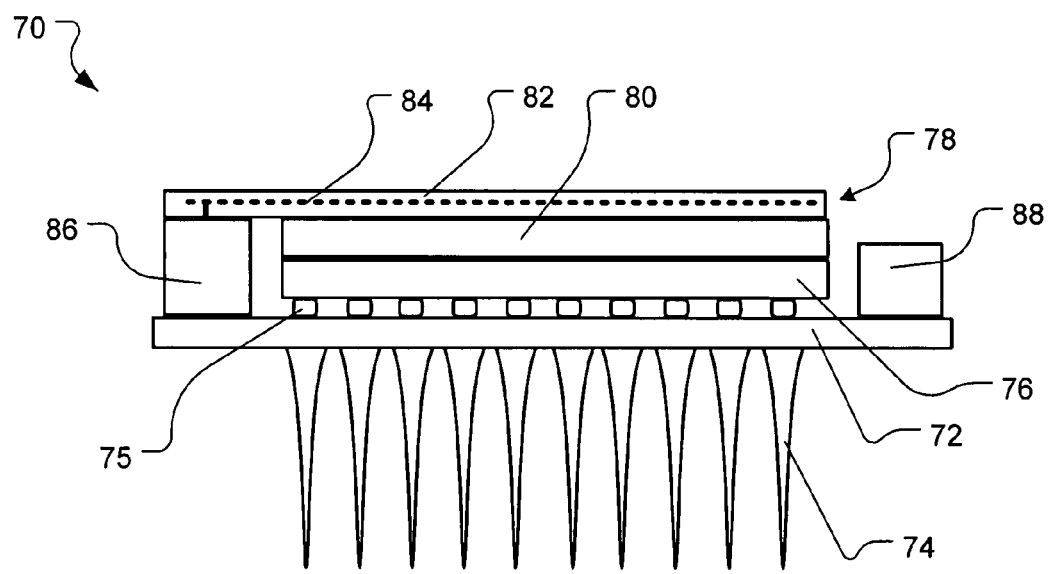
FIG. 5 is a side view of an integrated neural probe in accordance with an embodiment of the present invention.

There are various applications for an in-vivo implantable coil assembly as described herein. For example, an in-vivo implantable coil as described herein can be mounted to a neural interface assembly to form an integrated neural probe. FIG. 5 illustrates an integrated neural probe 70. The integrated neural probe includes an electrode array 72, for example, a Utah Electrode Array, as described in U.S. Pat. No. 5,215,088. The electrode array provides a plurality of needles 74 for interfacing to neural tissue. The electrode array also serves as a platform to which the other components of the neural probe are mounted. An integrated circuit chip 76 is attached to the electrode array (e.g. through solder bumps 75) and provides signal processing of neural signals transmitted and received by the electrode array. Mounted above the integrated circuit is the coil assembly 78, which comprises the ferrite platelet 80 and the polymer layer(s) 82 having the coil(s) 84 disposed therein. The coil assembly is electrically coupled to the integrated circuit via electrical routing traces provided by a spacer 86. For a coil assembly having a multilayer coil, individual coil layers may be selectively connected in either a series or parallel configuration via the routing traces provided by the spacer. Additional components 88 can also be surface mounted to the electrode array. For example, a capacitor may be used to form a resonant circuit with the coil. The entire electrode array may be encapsulated in a protective material (not shown).

The integrated neural probe 70 may be implanted into a living body. When implanted, the integrated neural probe can be powered by inductive coupling using a coil external to the living body. Energy can be received by the coil assembly 78, and electronically conditioned to power the integrated circuit 76. By providing wireless communications for information transmitted or received by the integrated neural probe, the integrated neural probe can be entirely enclosed within a living body, avoiding the need for maintaining an open incision while the integrated neural probe is used in vivo. Applications of integrated neural probes may include control of prosthetic devices, monitoring of internal body functions (e.g. glucose levels, respiration), artificial vision, machine control of involuntary muscle functions, etc.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of making an in-vivo implantable coil assembly comprising the steps of:
   a) coating a sacrificial separation layer onto a temporary substrate;
   b) depositing a polymer layer onto the separation layer;
   c) integrating a microchip with the polymer layer;
   d) fabricating a thin film coil on the polymer layer;
   e) forming electrical contacts on a top surface of the thin film coil;
   f) separating the polymer layer from the temporary substrate; and
   g) bonding the polymer layer to a ferrite platelet to form the in-vivo implantable coil assembly, wherein the ferrite platelet is between the planar coil and the microchip and is configured to shield a microchip from magnetic fields used to power the planar coil.

2. The method of claim 1, wherein the temporary substrate is reusable.

3. The method of claim 1, wherein the step of fabricating the thin film coil comprises the steps of:
   a) forming a first metallization layer on the polymer layer;
   b) patterning the first metallization layer to form a first coil layer;
   c) depositing a second polymer layer embedding the first coil layer;

d) forming a second metallization layer on the second polymer layer having at least two electrical interconnections to the first metallization layer; and e) patterning the second metallization layer to form a second coil layer.

4. The method of claim 3, wherein the steps of patterning the metallization layers are performed using photolithography.

5. The method of claim 1, wherein the step of fabricating the thin film coil comprises the step of depositing conductive material to form at least one coil layer onto the polymer layer.

6. The method of claim 1, wherein the step of separating the polymer layer from the substrate further comprises the step of chemically removing the separation layer.

7. The method of claim 1, wherein the polymer is a polyimide.

8. An in-vivo implantable coil assembly comprising:
a planar coil having at least one coil layer formed by conductive traces disposed in a polymer matrix and exposed electrical contacts for connection to the coil layer(s);
a ferrite platelet bonded to a surface of the polymer matrix, wherein the ferrite platelet is configured to shield a microchip from magnetic fields used to power the planar coil; and
a microchip integrated with the polymer matrix wherein the ferrite platelet is between the planar coil and the microchip.

9. The implantable coil assembly of claim 8 wherein the planar coil comprises a plurality of coil layers.

10. The implantable coil assembly of claim 9 wherein the exposed electrical contacts include at least one electrical contact for connection to each end of each coil layer to provide for alternative connection to the coil layers in a series and in a parallel arrangement.

11. The implantable coil assembly of claim 8 wherein the polymer is a polyimide.

12. The implantable coil assembly of claim 8 wherein the conductive traces include gold.

13. The implantable coil assembly of claim 8 wherein the ferrite platelet comprises a low temperature co-fired ceramic material.

14. The implantable coil assembly of claim 8 wherein the ferrite platelet comprises a plurality of colloidal ferrite particles within a non-conducting medium.

15. The implantable coil assembly of claim 14 wherein the non-conducting medium is a polymer.

16. The implantable coil assembly of claim 14 wherein the colloidal ferrite particles are nanoparticles.

17. The implantable coil assembly of claim 8 wherein the conductive trace width is 20 micrometers or less.

18. The implantable coil assembly of claim 8 wherein the conductive trace spacing is 20 micrometers or less.

19. The implantable coil assembly of claim 8 wherein the ferrite platelet has a relative permeability of 200 or greater.

20. The in-vivo implantable planar coil of claim 8 wherein the polymer matrix has a thickness within the range of about 5 micrometers to about 30 micrometers.

21. The in-vivo implantable planar coil of claim 8 wherein the ferrite platelet has a thickness within the range of about 100 micrometers to about 200 micrometers.

22. The implantable coil assembly of claim 8 wherein the conductive traces disposed in the polymer matrix are embedded within the polymer matrix.

23. The implantable coil assembly of claim 8 wherein the ferrite platelet is selected from the group consisting of iron oxides, Hematite ($Fe_2O_3$), Magnetite ($Fe_3O_4$), MnZn, NiZn, MgZn, barium ferrite, strontium ferrite, composites thereof, and combinations thereof.

24. A method of using an in-vivo implantable planar coil assembly in an integrated neural probe comprising the steps of:
a) providing a multilayer coil having a polymer substrate and bonded to a ferrite plate, a plurality of electrical contacts coupled to the multilayer coil and disposed on an upper surface of the multilayer coil to provide enable electrical connection to each layer of the multilayer coil; and
b) integrating a neural interface assembly with the polymer substrate to form an integrated neural probe, wherein the ferrite plate is between the multilayer coil and the neural interface assembly and is configured to shield the neural interface assembly from magnetic fields used to power the multilayer coil.

25. The method of claim 24, further comprising the step of selectively connecting individual layers of the multilayer coil in a series configuration.

26. The method of claim 24, further comprising the step of selectively connecting individual layers of the multilayer coil in a parallel configuration.

27. The method of claim 24, further comprising the step of implanting the integrated neural probe into a living body.

28. The method of claim 24, further comprising the step of inductively coupling power into the integrated neural probe via the multilayer coil.

* * * * *